United States Patent [19]

Wang

[11] Patent Number: 5,512,656
[45] Date of Patent: Apr. 30, 1996

[54] THYMOSIN ALPHA-1 DERIVATIVES

[75] Inventor: Su-Sun Wang, Belmont, Calif.

[73] Assignee: Alpha 1 Biomedicals, Inc., Bethesda, Md.

[21] Appl. No.: 246,572

[22] Filed: May 20, 1994

Related U.S. Application Data

[63] Continuation of Ser. No. 13,087, Feb. 3, 1993, abandoned.

[51] Int. Cl.$^6$ .............................. A61K 38/00; C07K 5/00; C07K 7/00; C07K 16/00
[52] U.S. Cl. ........................ 530/324; 530/325; 530/326; 530/327; 530/328; 530/329
[58] Field of Search ..................................... 530/324, 325, 530/326, 327, 328, 329; 514/12, 13, 14, 15, 16

[56] References Cited

U.S. PATENT DOCUMENTS

| | | |
|---|---|---|
| 4,079,127 | 3/1978 | Goldstein et al. . |
| 4,116,951 | 9/1978 | Wang . |
| 4,148,788 | 4/1979 | Wang . |
| 4,293,455 | 10/1981 | Merrifield et al. . |
| 4,855,407 | 8/1989 | Wang . |

FOREIGN PATENT DOCUMENTS

| | | |
|---|---|---|
| 0056594 | 1/1982 | European Pat. Off. . |
| 0075776 | 9/1982 | European Pat. Off. . |
| 2817082 | 11/1978 | Germany . |
| 3100974 | 1/1982 | Germany . |
| 8002560 | 11/1980 | WIPO . |

Primary Examiner—Christina Y. Chan
Assistant Examiner—A. M. Davenport
Attorney, Agent, or Firm—Rothwell Figg Ernst & Kurz

[57] ABSTRACT

A compound of the formula $$R_1\text{-}X\text{-}R_2\text{-}Y \quad (I)$$

wherein X is Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu, or a biologically active derivative or fragment thereof; $R_1$ is Ac or Z, wherein Ac is an acetyl group and Z is

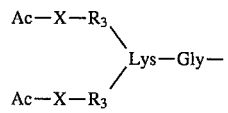

wherein Ac and X and are defined above; $R_2$ is Asn or Asp; $R_3$ is Asn or Asp; Y is —OH or —NH$_2$; with the proviso that when $R_1$ is Ac and $R_2$ is Asn, Y is -NH$_2$. The invention also applies to novel intermediates and precursors of compounds of formula (I) above.

12 Claims, No Drawings

THYMOSIN ALPHA-1 DERIVATIVES

This is a continuation of application Ser. No. 08/013,087, filed Feb. 3, 1993, now abandoned.

BACKGROUND OF THE INVENTION

1. Field of the Invention

The invention involves new synthetic compounds related to thymosin alpha-1.

2. Description of the Background Art

Thymosins are polypeptide immune modifiers derived from the thymus gland. Thymosins have been shown to induce T cell differentiation and enhance immunological functions.

A partially purified extract of calf thymus, called thymosin fraction 5, contains a number of peptide products of the thymus gland, including a component referred to as thymosin alpha-1.

Thymosin alpha-1 was initially isolated from thymosin fraction 5, and has been sequenced and chemically synthesized, U.S. Pat. Nos. 4,079,127; 4,148,788 and 4,855,407. Analogs of thymosin alpha-1 also have been produced, U.S. Pat. No. 4,116,951.

The sequence of thymosin alpha-1 is highly analogous in mice, calves and humans. Thymosin alpha- 1 has 28 amino acids and has been shown to have activity in modulating the immune system. The immunological activity of thymosin alpha-1 includes stimulation of alpha- and gamma-interferon production, increasing macrophage migration inhibitory factor production, inducing expression of T-cell markers, including interleukin-2 receptors, and improving T-cell helper cell activity.

There remains a need in the art for new synthetic compounds which can function like natural products of the thymus gland.

SUMMARY OF THE INVENTION

The present invention relates to a compound of the formula $$R_1\text{-}X\text{-}R_2\text{-}Y \qquad (I)$$

wherein X is Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu, or a biologically active derivative or fragment thereof; $R_1$ is Ac or Z, wherein Ac is an acetyl group and Z is

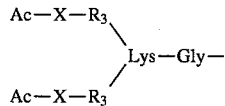

wherein Ac and X are as defined above; $R_2$ is Asn or Asp; $R_3$ is Asn or Asp; and Y is —OH or —$NH_2$; with the proviso that when $R_1$ is Ac and $R_2$ is Asn, Y is —$NH_2$. The invention also applies to novel intermediates and precursors of the compounds of formula (I).

DETAILED DESCRIPTION OF THE PREFERRED EMBODIMENTS

The compounds of the invention are derivatives of thymosin alpha-1, and are immune system modulators that are useful in the treatment of various diseases and indications which are responsive to immune system modulators. The immune potentiating compounds of the present invention can be utilized to reconstitute immune functions in immuno-deprived and immuno-depressed patients, and can be utilized for the treatment of immuno-deficiency diseases.

One specific example of an inventive compound of the formula (I) above is thymosin alpha-1 amide, wherein $R_1$ is acetyl, $R_2$ is Asn and Y is —$NH_2$. Another example of a compound in accordance with the present invention is [$Asp^{28}$]-thymosin alpha-1, wherein $R_1$ is acetyl, $R_2$ is Asp and Y is —OH. The invention is also applicable to thymosin alpha-1 trimers, wherein $R_1$ is Z as defined above.

The invention also includes novel intermediates and precursors of compounds in accordance with formula (I) above.

Examples of intermediates and precursors include compounds comprised of the formula:

$$X_2\text{-Val-Glu-Glu-Ala-Glu-}R_2 \qquad (II)$$

wherein $R_2$ is Asn or Asp; and wherein $X_2$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val, Asp-Leu-Lys-Glu-Lys-Lys-Glu-Val, Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val, Ser-Ser-Glu-Ile-Thr-Thr-Lys-Asp-Leu-Lys-Glu-Lys-Lys-Glu-Val, Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr-Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val, Ser-Asp-Ala-Ala-Val-Asp-Thr-Ser-Ser-Glu-Ile-Thr-Thr-Lys-Asp-Leu-Lys-Glu-Lys-Lys-Glu-Val, Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, Lys-Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, or Z-Ser-Asp-Ala-Ala-Val-Asp-Thr-Ser-Ser-Glu-Ile-Thr-Thr-Lys-Asp-Leu-Lys-Glu-Lys-Lys-Glu-Val, wherein Z is represented by the formula:

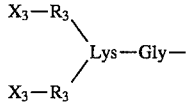

wherein $R_3$ is Asn or Asp and $X_3$ is Glu, Ala-Glu, Glu-Ala-Glu, Glu-Glu-Ala-Glu, Val-Glu-Glu-Ala-Glu, or $X_4$-Val-Glu-Glu-Ala-Glu, wherein $X_4$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val, Asp-Leu-Lys-Glu-Lys-Lys-Glu-Val, Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val, Ser-Ser-Glu-Ile-Thr-Thr-Lys-Asp-Leu-Lys-Glu-Lys-Lys-Glu-Val, Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr- Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val, Ser-Asp-Ala-Ala-Val-Asp-Thr-Ser-Ser-Glu-Ile-Thr-Thr-Lys-Asp-Leu-Lys-Glu-Lys-Lys-Glu-Val; with the proviso that when $R_2$ is Asn, $X_2$ is Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, Lys-Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, or Z-Ser-Asp-Ala-Ala-Val-Asp-Thr-Ser-Ser-Glu-Ile-Thr-Thr-Lys-Asp-Leu-Lys-Glu-Lys-Lys-Glu-Val.

In embodiments in which $X_2$ includes the group Z, $R_3$ preferrably is Asn.

The compounds, intermediates and precursors of the present invention can be provided by any suitable method, such as by solid phase peptide synthesis.

The invention is further illustrated by the following examples, which are not intended to be limiting.

EXAMPLE 1

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-NH$_2$ (Thymosin alpha-1 amide)

1.0 gm of methylbenzyhydrylamine resin, provided in accordance with Example 1 of U.S. Pat. No. 4,855,407, incorporated herein by reference, was placed in a peptide synthesis flask equipped with sintered glass filter at the bottom and an over head mechanical stirrer at the top. The resin was washed with 20 volumes of 10% triethylamine in methylene chloride and stirred with a fresh portion of the same solution for 10 minutes. The neutralized methylbenzhydrylamine resin was then allowed to react with 1.5 mmol of Boc-L-asparagine (0.35 g), 3.0 mmol of 1-hydroxybenzotriazole monohydrate (0.46 g) and 1.5 mmol of N,N'-dicyclohexylcarbodiimide (0.309 g) in 15 mL of N,N-dimethylformamide overnight to form Boc-L-asparaginyl methylbenzhydrylamine resin. The amino acid resin was acetylated with 2 mmol of acetic acid (0.12 mL) and 1.5 mmol of N,N'-dicyclohexylcarbodiimide for one hour in 20 mL methylene chloride in order to eliminate a very slightly positive reaction to ninhydrin test.

The solid phase peptide synthesis was then continued by performing the following steps wherein in each cycle one amino acid was incorporated sequencially into the growing peptide chain on the resin (20 volumes of solvent or reagents was used for each washing unless otherwise indicated. All the amino acid derivatives utilized were of L-configuration unless otherwise stated):

(1) prewash the resin with 50% trifluoroacetic acid in methylene chloride;

(2) stir for 30 minutes with 50% trifluoroacetic acid in methylene chloride;

(3) wash three times with methylene chloride;

(4) prewash with 10% triethylamine in methylene chloride;

(5) stir for 5 minutes with 10% triethylamine in methylene chloride;

(6) wash three times with methylene chloride;

(7) stir for 120 minutes with 1.5 mmol each of Boc-Glu(OBzl)-OH and N,N'-dicyclohexylcarbodiimide in methylene chloride;

(8) wash twice with 50% isopropyl alcohol in methylene chloride;

(9) wash three times with methylene chloride;

(10) test for ninhydrin color reaction; if positive, repeat steps 7–10; if negative, go to the next synthetic cycle.

The synthetic cycle was then repeated using the following Boc-amino acids sequentially and one at a time in step 7 of each cycle; Boc-Ala-OH, Boc-Glu(OBzl)-OH, Boc-Glu-(OBzl)-OH, Boc-Val-OH, Boc-Val-OH, Boc-Glu(OBzl)-OH, Boc-Lys(ClZ)-OH, Boc-Lys(ClZ)-OH, Boc-Glu-(OBzl)-OH, Boc-Lys(ClZ)-OH, Boc-Leu-OH, Boc-Asp(OBzl)-OH, Boc-Lys(ClZ)-OH, Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Ser(Bzl)-OH and CH$_3$COOH. After the completion of all the synthetic cycles, the protected thymosin alpha-1 amide-MBHA-resin so obtained, Ac-Ser-(Bzl)-Asp(OBzl)-Ala-Ala-Val-Asp(OBzl)-Thr(Bzl)-Ser-(Bzl)-Ser(Bzl)-Glu(OBzl)-Ile-Thr(Bzl)-Thr(Bzl)-Lys(ClZ)-Asp(OBzl)-Leu-Lys(ClZ)-Glu(OBzl)-Lys(ClZ)-Lys(ClZ)-Glu(OBzl)-Val-Val-Glu(OBzl)-Glu(OBzl)-Ala-Glu(OBzl)-Asn-HN-CH(Ph-CH$_3$)-resin, weighed 2.7 g.

For deprotection as well as cleavage, part (1.0 g) of this peptide resin was mixed with 2 mL of anisole and stirred at 0° C. in liquid hydrogen fluoride for 60 minutes. After removal of the excess acid, the residue was washed with dry ether several times and the residue extracted with 50 mL 4% ammonium acetate followed by 25 mL distilled water. The combined extracts were concentrated to a smaller volume (10–12 mL), desalted on a Sephadex G-10 column (2.6×85 cm, 0.1M HOAc) and lyophilized to give 0.37 g of crude thymosin alpha-1 amide.

The major portion of the crude peptide (0.347 g) obtained above was purified by semi-preparative HPLC on a Vydac C$_{18}$ column (2.2×25 cm, 10μ), eluted with a linear gradient of 2.5%–9.0% isopropanol (pH 6 potassium phosphate buffer), at a flow rate of 5.5 mL/min, monitored at 234 nm. Each peptide fraction was checked by an analytical HPLC. Only those fractions that showed the purity of 98% or above were pooled, desalted on Sephadex G-10 column and lyophilized to yield 0.0767 g of desired product, thymosin alpha-1 amide.

Analytical HPLC showed that the product was homogeneous and it migrated slightly slower than thymosin alpha-1. When thymosin alpha-1 amide was mixed with thymosin alpha-1 and chromatographed in analytical HLPC, the two compounds were well resolved from each other in the analytical HPLC system employed. Molecular weight determination by FAB mass spectrometry indicated that the material had correct molecular weight of MH$^+$=3108 (calculated MW=3107.3). Amino acid analyses of the acid hydrolyzates (24 hours and 100 hours) indicated that the peptide had the expected amino acid ratios: 6N HCl 110°, 24 hr; Asp, 3 86; Thr, 2.90; Ser, 2.63; Glu, 6.14; Ala, 2.86; Val, 2.23; Ile, 0.96; Leu, 1.03; Lys, 4.12. 6N HCl, 110°, 100 hr; Asp, 4.09; Thr, 2.90; Ser, 1.98; Glu, 6.45; Ala, 3.00; Val, 2.95; Ile, 0.98; Leu, 1.04; Lys, 4.11.

EXAMPLE 2

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asp-OH ([Asp$^{28}$]-Thymosin alpha-1)

1.0 gm of Boc-Aspartic acid β-benzyl ester resin (0.5 mmol/g) was placed in a peptide synthesis flask and the solid phase peptide synthesis performed by carrying out the following steps wherein in each cycle one amino acid was incorporated sequencially into the growing peptide chain on the resin. All amino acid derivatives used were of L-configuration unless otherwise indicated:

(1) prewash with 50% trifluoroacetic acid in methylene chloride;

(2) stir for 30 minutes with 50% trifluoroacetic acid in methylene chloride;

(3) wash three times with methylene chloride;

(4) prewash with 10% triethylamine in methylene chloride;

(5) stir for 5 minutes with 10% triethylamine in methylene chloride;

(6) wash three times with methylene chloride;

(7) stir for 150 minutes with 1.5 mmol each of Boc-Glu(OBzl)-OH and N,N'-dicyclohexylcarbodiimide in methylene chloride;

(8) wash twice with 50% isopropyl alcohol in methylene chloride;

(9) wash three times with methylene chloride;

(10) test for ninhydrin color reaction; if positive, repeat steps 7–10; if negative go to the next synthetic cycle.

The synthetic cycle was then repeated using the following Boc-amino acids sequencially and one at a time in step 7 of each cycle: Boc-Ala-OH, Boc-Glu(OBzl)-OH, Boc-Glu-(OBzl)-OH, Boc-Val-OH, Boc-Val-OH, Boc-Glu(OBzl)-OH, Boc-Lys(ClZ)-OH, Boc-Lys(ClZ)-OH, Boc-Glu-(OBzl)-OH, Boc-Lys(ClZ)-OH, Boc-Leu-OH, Boc-Asp(OBzl)-OH, Boc-Lys(ClZ)-OH, Boc-Thr(Bzl)-OH, Boc-Thr(Bzl)-OH, Boc-Ile-OH, Boc-Glu-(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Ser(Bzl)-OH and CH$_3$COOH. Upon completion of all the synthetic cycles, the protected [Asp$^{28}$]-thymosin alpha-1-resin with the structure of Ac-Ser(Bzl)-Asp(OBzl)-Ala-Ala-Val-Asp(OBzl)-Ser(Bzl)-Ser-(Bzl)-Glu(OBzl)-Ile-Thr(Bzl)-Thr(Bzl)-Lys(ClZ)-Asp(OBzl)-Leu-Lys(ClZ)-Glu(OBzl)-Lys(ClZ)-Lys(ClZ)-Glu(OBzl)-Val-Val-Glu(OBzl)-Ala-Glu(OBzl)-Asp(OBzl)-OCH$_2$C$_6$H$_4$-Resin, weighed 2.08 g.

Part (1.0 g) of the protected peptide resin obtained above was stirred with 10 mL of anhydrous liquid hydrogen at 0° C., in the presence of 2 mL anisole, for 60 minutes. The excess acid was evaporated off and the residue washed quickly twice with dry ether. Peptide materials were extracted into 4% ammonium acetate (50 mL) followed by distilled water (25 mL). The combined extracts were concentrated to a smaller volume and desalted on a Sephadex G-10 column (2.6×85 cm, 01.M HOAc). Lyophilization of the peptide peak afforded 0.327 g of crude product.

0.27 g of this crude peptide was purified on a Hamilton PRP-1 column (2.15×25 cm, 10μ particle size, 3% and then 6% acetonitrile in pH 6, potassium phosphate buffer). The fractions were analyzed by analytical HPLC and those fractions containing desired material were pooled and desalted on Sephadex G-10 column. Lyophilization of the main peak yielded 35 mg of [Asp$^{28}$]-thymosin alpha-1. On analytical HPLC, this material showed a slightly faster mobility than thymosin alpha-1 as expected due to its slightly stronger polarity and slightly higher acidity. FAB mass spectrometric analysis showed that MH$^+$=3110 (calculated MW=3109.3). Amino acid analyses of the acid hydrolyzates indicated that the product had the correct amino acid composition; 6N HCl, 110°, 24 hr; Asp, 4.00; Thr, 3.10; Ser, 2.54; Glu, 5.85; Ala, 2.80; Val, 1.70; Ile, 0.95; Leu, 1.03; Lys, 3.76 6N HCl, 110°, 100 hr; Asp, 4.00; Thr, 3.03; Ser, 2.21; Glu, 6.12; Ala, 2.81; Val, 3.04; Ile, 0.96; Leu, 1.09; Lys, 4.17.

EXAMPLE 3

(Thymosin Alpha-1 Trimer)

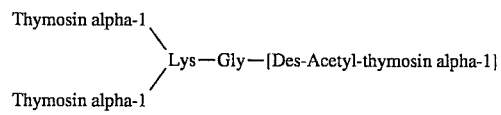

2.0 gm of methylbenzhydrylamine resin (0.5 mmol/g, 1.0 mmol) was placed in the peptide synthesis flask and washed three times with methylene chloride followed by one time with 10% triethylamine in methylene chloride. The resin was then stirred 10 minutes with 10% triethylamine in methylene chloride and washed three times with methylene chloride. The neutralized resin was then reacted with 3 mmol each of Boc-aspartic acid alpha-benzyl ester and N,N'-dicyclohexylcarbodiimide in methylene chloride for 75 minutes to form Boc-aspartic acid alpha-benzyl ester β-amide of methylbenzhydrylamine resin with the structure of Boc-Asp[ HN-CH(C$_6$H$_4$-CH$_3$)-Resin]-OBzl. The Boc-amino acid resin was further treated with 4 mmol of acetic acid and 3 mmol of N,N'-dicyclohexylcarbodiimide in methylene chloride for 180 minutes in order to remove a very slightly positive reaction to ninhydrin test.

The solid phase synthesis was continued by carrying out the following steps wherein in each cycle one specific amino acid was incorporated into the growing peptide chain anchored on the resin. [The peptide chain on the resin initially was a single linear structure until the glycine residue at number 28 cycle and N$^\alpha$,N$^\epsilon$-Di-Boc-lysine at number 29 cycle were incorporated. It then branched into two parallel chains hinged on the same lysine residue starting from cycle number 30 where two units of Boc-asparagine residue were added into two chains simultaneously]. In substantially the same manner as described in the above examples, 20 volumes of solvents or reagents were used in each step:

(1) prewash with 50% trifluoroacetic acid in methylene chloride;

(2) stir for 30 minutes with 50% trifluoroacetic acid in methylene chloride;

(3) wash three times with methylene chloride;

(4) prewash with 10% triethylamine in methylene chloride;

(5) stir for 5 minutes with 10% triethylamine in methylene chloride;

(6) wash three times with methylene chloride;

(7) stir for 120 minutes with 3 mmol each of Boc-Glu(OBzl)-OH and N,N'-dicyclohexylcarbodiimide in methylene chloride;

(8) wash twice with 50% isopropyl alcohol in methylene chloride;

(9) wash three times with methylene chloride;

(10) test for ninhydrin color reaction; if positive, repeat steps 7–10; if negative go to the next synthetic cycle.

The synthetic cycle was then repeated using the following Boc-amino acids sequencially and one at a time in step 7 of each cycle: Boc-Ala-OH, Boc-Glu(OBzl)-OH, Boc-Glu-(OBzl)-OH, Boc-Val-OH, Boc-Val-OH, Boc-Glu(OBzl)-OH, Boc-Lys(ClZ)-OH, Boc-Lys(ClZ)-OH, Boc-Glu-(OBzl)-OH, Boc-Lys(ClZ)-OH, Boc-Leu-OH, Boc-Asp(OBzl)-OH, Boc-Lys(ClZ)-OH, Boc-Thr(Bzl)-OH, Boc-Thr(Bzl)-OH, Boc-Ile-OH, Boc-Glu-(OBzl)-OH, Boc-Ser(Bzl)-OH, Boc-Ser(Bzl)-OH, Boc-Thr(Bzl)-OH, Boc-Asp(OBzl)-OH, Soc-Val-OH, Soc-Ala-OH, Boc-Ala-OH, Boc-Asp(OBzl)-OH, Boc-Ser(Bzl)-OH. At this point, 3.96 g of peptide resin was removed from the peptide synthesis flask and the remaining 1.96 g peptide resin allowed to continue the synthesis by using Boc-Gly-OH in one cycle and then $N^{\alpha}$-Boc-$N^{\xi}$-Boc-Lys-OH in step 7 of the next cycle to introduce the branching off point for the peptide chain assembly. The synthesis was further continued with Boc-Asn-OH, Boc-Glu(OBzl), Boc-Ala-OH, Boc-Glu(OBzl)-OH, Boc-Glu(OBzl)-OH, Boc-Val-OH, Boc-Val-OH, Boc-Glu(OBzl)-OH, Boc-Lys(ClZ)-OH, Boc-Lys(ClZ)-OH, Boc-Glu(OBzl)-OH, Boc-Lys(ClZ)-OH, Boc-Leu-OH, Boc-Asp(OBzl)-OH, Boc-Lys(ClZ)-OH, Boc-Thr(Bzl)-OH, Boc-Thr(Bzl)-OH, Boc-Ile-OH, Boc-Glu(OBzl)-OH, Boc-Ser(Bzl)-OH, Boc-Ser(Bzl)-OH, Boc-Thr(Bzl)-OH, Boc-Asp(OBzl)-OH, Boc-Val-OH, Boc-Ala-OH, Boc-Ala-OH, Boc-Asp(OBzl)-OH, Boc-Ser(Bzl)-OH, and $CH_3COOH$. The completed protected thymosin alpha-1 trimer-resin with the structure of:

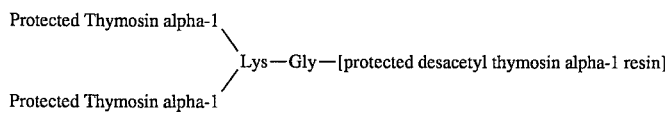

weighed 2.64 g.

Part (0.91 g) of the protected thymosin alpha-1 trimer-resin obtained above was stirred with 10 mL of anhydrous hydrogen fluoride at 0° C., in the presence of 2 mL anisole for 60 minutes. Upon removal of the excess acid, the residue was washed twice with dry ether and the peptide material extracted into 20 mL of 4% ammonium acetate followed by 10 mL distilled water. The combined extracts were concentrated to about 10 mL and desalted on the Sephadex G-10 column (2.6×85 cm, 0.1M HOAc). The material under the major peak was collected and lyophilized to give 0.35 g or crude thymosin alpha-1 trimer.

Purification of the crude sample (0.34 g) on a Hamilton PRP-1 reversed phase polystyrene column (2.15×250 mm, 10μ particle size) eluting with a linear gradient of 8.5%–20% acetonitrile in pH 6 potassium phosphate, at a flow rate of 5.45 mL/min provided a fraction which on desalting on the Sephadex G-10 column yielded 0.045 g of desired thymosin alpha-1 trimer. It was shown to be homogeneous on analytical HPLC and had the expected amino acid composition 6N HCl, 110°, 24 hr; Asp, 11.83; Thr, 9.17; Ser, 8.00; Glu, 18.16; Gly, 0.97; Ala, 8.68; Val, 6.54; Ile, 3.04; Leu, 3.18; Lys, 12.58. 6N HCl, 110°, 100 hr; Asp, Asp, 12.14; Thr, 9.45; Ser, 6.47; Glu, 17.86; Gly, 1.07; Ala, 8.51; Val, 8.79; Ile, 2.89; Leu, 3.11; Lys, 13.11. ES mass spectrometry indicated that the material had correct molecular weight of 9432.13 (calculated MW=9432.1).

Since many modifications, variations and changes in detail may be made to the described embodiments, it is intended that all matter in the foregoing description be interpreted as illustrative and not in a limiting sense.

I claim:

1. A compound of the formula:

$$R_1\text{-}X\text{-}R_2\text{-}Y \qquad (I)$$

wherein X is Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu, $R_1$ is Ac or Z, wherein Ac is an acetyl group and Z is $$\begin{array}{c} Ac-X-R_3 \\ \diagdown \\ \diagup \\ Ac-X-R_3 \end{array} Lys-Gly-$$

wherein Ac and X are as defined above; $R_2$ is Asp or $R_3$; $R_3$ is Asn; and Y is —OH; with the proviso that only when $R_3$ is present does $R_2$ equal $R_3$.

2. The compound of claim 1 wherein $R_1$ is Z, $R_3$ is Asn, $R_2$ is Asn, and Y is —OH.

3. The compound, comprised of the formula:

$$X_2\text{-Val-Glu-Glu-Ala-Glu-}R_2 \qquad (II)$$

wherein $R_2$ is Asp or $R_3$; and wherein $X_2$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val, Asp-Leu-Lys-Glu-Lys-Lys-Glu-Val, Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val, Ser-Ser-Glu-Ile-Thr-Thr-Lys-Asp-Leu-Lys-Glu-Lys-Lys-Glu-Val, Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr-Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val, Ser-Asp-Ala-Ala-Val-Asp-Thr-Ser-Ser-Glu-Ile-Thr-Thr-Lys-Asp-Leu-Lys-Glu-Lys-Lys-Glu-Val, Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, Lys-Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, or Z-Ser-Asp-Ala-Ala-Val-Asp-Thr-Ser-Ser-Glu-Ile-Thr-Thr-Lys-Asp-Leu-Lys-Glu-Lys-Lys-Glu-Val, wherein Z is represented by the formula:

$$\begin{array}{c} X_3-R_3 \\ \diagdown \\ \diagup \\ X_3-R_3 \end{array} Lys-Gly-$$

wherein $R_3$ is Asn, and $X_3$ is Glu, Ala-Glu, Glu-Ala-Glu, Glu-Glu-Ala-Glu, Val-Glu-Glu-Ala-Glu, or $X_4$-Val-Glu-Glu-Ala-Glu, wherein $X_4$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val, Asp-Leu-Lys-Glu-Lys-Lys-Glu-Val, Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val, Ser-Ser-Glu-Ile-Thr-Thr-Lys-Asp-Leu-Lys-Glu-Lys-Lys-Glu-Val, Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr-Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val, Ser-Asp-Ala-Ala-Val-Asp-Thr-Ser-Ser-Glu-Ile-Thr-Thr-Lys-Asp-Leu-Lys-Glu-Lys-Lys-Glu-Val; with the proviso that when $R_2$ is Asn, $X_2$ is Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, Lys-Gly-Ser-Asp-Ala-Ala-Val-Asp-Thr-Ser-Ser-Glu-Ile-Thr-Thr-Lys-Asp-Leu-Lys-Glu-Lys-Lys-Glu-Val, or Z-Ser-Asp-Ala-Ala-Val-Asp-Thr-Ser-Ser-Glu-Ile-Thr-Thr-Lys-Asp-Leu-Lys-Glu-Lys-Lys-Glu-Val, and with the further proviso that $R_2=R_3$ only when Z is present.

4. The compound of claim 3, wherein $X_2$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val or Asp-Leu-Lys-Glu-Lys-Lys-Glu-Val.

5. The compound of claim 3, wherein $X_2$ is Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val or Ser-Ser-Glu-Ile-Thr-Thr-Lys-Asp-Leu-Lys-Glu-Lys-Lys-Glu-Val.

6. The compound of claim 3, wherein $X_2$ is Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr-Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val, or Ser-Asp-Ala-Ala-Val-Asp-Thr-Ser-Ser-Glu-Ile-Thr-Thr-Lys-Asp-Leu-Lys-Glu-Lys-Lys-Glu-Val.

7. The compound of claim 3, wherein $X_2$ is Gly-Ser-Asp-Ala-Ala-Val-Asp-Thr-Ser-Ser-Glu-Ile-Thr-Thr-Lys-Asp-Leu-Lys-Glu-Lys-Lys-Glu-Val.

8. The compound of claim 3, wherein $X_2$ is Lys-Gly-Ser-Asp-Ala-Ala-Val-Asp-Thr-Ser-Ser-Glu-Ile-Thr-Thr-Lys-Asp-Leu-Lys-Glu-Lys-Lys-Glu-Val.

9. The compound of claim 3, wherein $R_2=R_3$ $X_2$ is Z-Ser-Asp-Ala-Ala-Val-Asp-Thr-Ser-Ser-Glu-Ile-Thr-Thr-Lys-Asp-Leu-Lys-Glu-Lys-Lys-Glu-Val, wherein Z is represented by the formula:

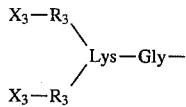

wherein $R_3$ is Asn and $X_3$ is Glu, Ala-Glu, Glu-Ala-Glu, Glu-Glu-Ala-Glu or Val-Glu-Glu-Ala-Glu.

10. The compound of claim 3, wherein $X_2$ is Z-Ser-Asp-Ala-Ala-Val-Asp-Thr-Ser-Ser-Glu-Ile-Thr-Thr-Lys-Asp-Leu-Lys-Glu-Lys-Lys-Glu- Val, wherein Z is represented by the formula:

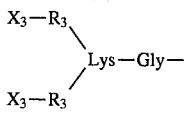

wherein $R_3$ is Asn and $X_3$ is $X_4$-Val-Glu-Glu-Ala-Glu, wherein $X_4$ is Val, Glu-Val, Lys-Glu-Val, Lys-Lys-Glu-Val, Glu-Lys-Lys-Glu-Val, Lys-Glu-Lys-Lys-Glu-Val, Leu-Lys-Glu-Lys-Lys-Glu-Val or Asp-Leu-Lys-Glu-Lys-Lys-Glu-Val.

11. The compound of claim 3, wherein $X_2$ is Z-Ser-Asp-Ala-Ala-Val-Asp-Thr-Ser-Ser-Glu-Ile-Thr-Thr-Lys-Asp-Leu-Lys-Glu-Lys-Lys-Glu- Val, wherein Z is represented by the formula:

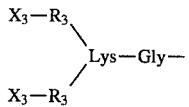

wherein $R_3$ is Asn and $X_3$ is $X_4$-Val-Glu-Glu-Ala-Glu, wherein $X_4$ is Lys-Asp-Leu-Lys-Glu-Lys-Lys-Glu-Val, Thr-Lys-Asp-Leu-Lys-Glu-Lys-Lys-Glu-Val, Thr-Thr-Lys-Asp-Leu-Lys-Glu-Lys-Lys-Glu-Val, Ile-Thr-Thr-Lys-Asp-Leu-Lys-Glu-Lys-Lys-Glu-Val, Glu-Ile-Thr-Thr-Lys-Asp-Leu-Lys-Glu-Lys-Lys-Glu-Val, Ser-Glu-Ile-Thr-Thr-Lys-Asp-Leu-Lys-Glu-Lys-Lys-Glu-Val or Ser-Ser-Glu-Ile-Thr-Thr-Lys-Asp-Leu-Lys-Glu-Lys-Lys-Glu-Val.

12. The compound of claim 3, wherein $X_2$ is Z-Ser-Asp-Ala-Ala-Val-Asp-Thr-Ser-Ser-Glu-Ile-Thr-Thr-Lys-Asp-Leu-Lys-Glu-Lys-Lys-Glu- Val, wherein Z is represented by the formula:

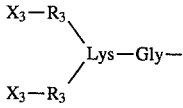

wherein $R_3$ is Asn and $X_3$ is $X_4$-Val-Glu-Glu-Ala-Glu, wherein $X_4$ is Thr-Ser-Ser-Glu-Ile-Thr-Thr-Lys-Asp-Leu-Lys-Glu-Lys-Lys-Glu-Val, Asp-Thr-Ser-Ser-Glu-Ile-Thr-Thr-Lys-Asp-Leu-Lys-Glu-Lys-Lys-Glu-Val, Val-Asp-Thr-Ser-Ser-Glu-Ile-Thr-Thr-Lys-Asp-Leu-Lys-Glu-Lys-Lys-Glu-Val, Ala-Val-Asp-Thr-Ser-Ser-Glu-Ile-Thr-Thr-Lys-Asp-Leu-Lys-Glu-Lys-Lys-Glu-Val, Ala-Ala-Val-Asp-Thr-Ser-Ser-Glu-Ile-Thr-Thr-Lys-Asp-Leu-Lys-Glu-Lys-Lys-Glu-Val, Asp-Ala-Ala-Val-Asp-Thr-Ser-Ser-Glu-Ile-Thr-Thr-Lys-Asp-Leu-Lys-Glu-Lys-Lys-Glu-Val or Ser-Asp-Ala-Ala-Val-Asp-Thr-Ser-Ser-Glu-Ile-Thr-Thr-Lys-Asp-Leu-Lys-Glu-Lys-Lys-Glu-Val.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Asp  Ala  Ala  Val  Asp  Thr  Ser  Ser  Glu  Ile  Thr  Thr  Lys  Asp  Leu
1                   5                        10                       15
Lys  Glu  Lys  Lys  Glu  Val  Val  Glu  Glu  Ala  Glu
               20                  25
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Lys  Gly  Ser  Asp  Ala  Ala  Val  Asp  Thr  Ser  Ser  Glu  Ile  Thr  Thr  Lys
1                   5                        10                       15
Asp  Leu  Lys  Glu  Lys  Lys  Glu  Val  Val  Glu  Glu  Ala  Glu  Asn
               20                  25                       30
```

( 2 ) INFORMATION FOR SEQ ID NO:3:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Lys  Gly  Ser  Asp  Ala  Ala  Val  Asp  Thr  Ser  Ser  Glu  Ile  Thr  Thr
1                   5                        10                       15
Lys  Asp  Leu  Lys  Glu  Lys  Lys  Glu  Val  Val  Glu  Glu  Ala  Glu  Asp
               20                  25                       30
```

( 2 ) INFORMATION FOR SEQ ID NO:4:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ser  Asp  Ala  Ala  Val  Asp  Thr  Ser  Ser  Glu  Ile  Thr  Thr  Lys  Asp  Leu
1                   5                        10                       15
```

```
      Lys  Glu  Lys  Lys  Glu  Val  Val  Glu  Glu  Ala  Glu  Asn
                      20                        25
```

( 2 ) INFORMATION FOR SEQ ID NO:5:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
      Ser  Asp  Ala  Ala  Val  Asp  Thr  Ser  Ser  Glu  Ile  Thr  Thr  Lys  Asp  Leu
      1                   5                        10                       15

Lys  Glu  Lys  Lys  Glu  Val  Val  Glu  Glu  Ala  Glu  Asp
                      20                        25
```